United States Patent [19]  [11] 3,959,429
Benning  [45] May 25, 1976

[54] METHOD OF MAKING A RETENTION CATHETER AND MOLDING A TIP THEREON

[75] Inventor: Calvin J. Benning, Mahwah, N.J.

[73] Assignee: International Paper Company, New York, N.Y.

[22] Filed: Feb. 3, 1975

[21] Appl. No.: 546,297

[52] U.S. Cl. .............................. 264/155; 264/156; 264/250; 264/254; 264/255; 264/261; 264/263; 264/271; 264/294; 264/328; 264/336
[51] Int. Cl.² ...................... B29C 5/00; B29H 3/08
[58] Field of Search ............ 264/248, 250, 259, 271, 264/275, 294, 296, 328, 254, 262, 263, 267, 279, 329, 155, 156, 261, 255; 128/349 B, 349 R, 349 BV

[56] References Cited
UNITED STATES PATENTS
| | | | |
|---|---|---|---|
| 3,547,126 | 12/1970 | Birtwell | 128/349 B |
| 3,832,253 | 8/1974 | DiPalma et al. | 128/349 |
| 3,865,666 | 2/1975 | Shoney | 264/254 X |

*Primary Examiner*—Willard E. Hoag
*Attorney, Agent, or Firm*—Richard M. Barnes

[57] ABSTRACT

A method of making a retention catheter of the Foley type comprising the steps of insert molding a tip onto a catheter shaft with the proximal end of balloon attached thereto and simultaneously insert bonding the distal end of the balloon into the catheter tip.

11 Claims, 4 Drawing Figures

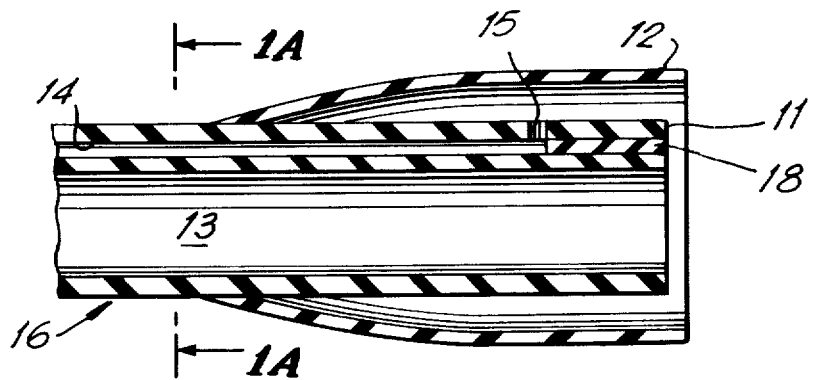
FIG. 1
FIG. 1A
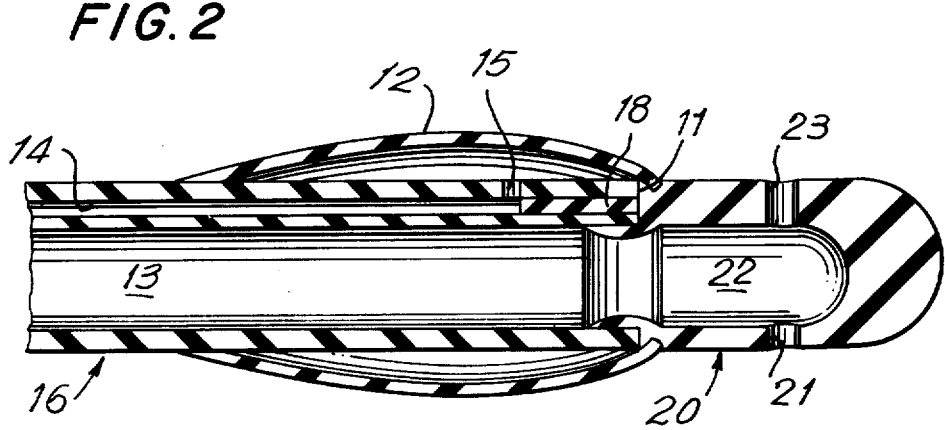
FIG. 2

METHOD OF MAKING A RETENTION CATHETER AND MOLDING A TIR THEREON

BACKGROUND OF THE INVENTION

1. Field to Which the Invention Pertains

Well known to physicians is the fact that individuals may, for a variety of reasons, lose control of their urinary function. Although the reasons for the loss of urinary control are manifold, the consequent treatment is a rather well accepted medical practice which involves inserting a tube or catheter up the urinary passage until the remote or distal end is located within the bladder. The near or proximal end of the catheter remains outside of the body and there is thus provided a path or means through which the bladder may drain. Once a catheter has been passed through the urinary tract and inserted into the bladder, it is generally both medically desirable and necessary to have the catheter retained in the urinary tract with the distal end of the catheter positioned within the bladder. Catheters which are designed for such a function are called urinary retention catheters and are generally provided with some means to promote retention. Typically, this retention capability is provided by including an inflatable balloon at the distal end of the catheter. During insertion, the balloon is deflated. After the distal end of the catheter is positioned within the bladder, the balloon is inflated by passing a fluid, typically water, through a passage within the catheter which is referred to as an inflation lumen. When the balloon is inflated, the inflation lumen is sealed and the inflated balloon within the bladder insures retention. Thereafter, the bladder may drain through a second passage within the catheter, i.e., the drainage lumen.

There are a number of medical procedures which involve the use of catheters and, as a result, catheters are generally referred to by a name associated with their function, e.g., urinary catheters, tracheal catheters, venous catheters, etc. While all such catheters must be fabricated so as to insure the safety and comfort of the patient, the physiological demands imposed upon a urinary retention catheter are particularly severe and appear to result in conflicting design criteria. For example, the comfort of the patient dictates that a urinary retention catheter be as soft and as flexible as possible. On the other hand, from a structural point of view, such a catheter must be sufficiently rigid to insure that as it traverses the urinary tract, the catheter tube will not bend to an extend which results in occluding or reducing the size of the drainage lumen and the inflation lumen. Similarly, it is clearly desirable that the outer diameter of the catheter be as small as possible while the diameter of the drainage lumen be as large as possible. However, the maximum outer diameter of the catheter is substantially defined by the diameter of the urinary tract and the comfort of the patient while the contractive forces which are exerted on the catheter by the urinary tract substantially define a maximum wall thickness between the drainage lumen and the exterior of the catheter.

Of substantial concern to both the patient and the physician is the balloon and its proper inflation. After the catheter is inserted, it is desirable that the balloon be so constructed and arranged that it can be inflated with a minimum inflation pressure. Such an objective is desirable because the maximum inflation pressure required to inflate a balloon will be the determining factor with respect to the minimum wall thickness surrounding the inflation lumen. Since one desires to maximize the size of the drainage lumen and since the area occupied by the inflation lumen diminishes the size of the drainage lumen, it follows that one wishes to utilize a minimum wall thickness for the inflation lumen and, therefore, the balloon construction should be such as to require a minimum pressure for inflation. While one may construct a urinary retention catheter having a balloon which will inflate with a minimum pressure, the resulting structure may, and often does, possess undesirable features. For example, to achieve a low inflation pressure, a soft and pliant material may be used for the balloon. However, from a manufacturing point of view, it is generally most economical to fabricate the balloon as an integral part of the catheter tip and, thus, the catheter tip will also be soft and pliant. Constructions of this type, which are known to the prior art, unfortunately possess certain disadvantages which are discussed hereinafter.

Finally, urinary retention catheters must not only meet or exceed the various medical and patient oriented criteria discussed above but, in addition, such a catheter must be of a construction which lends itself to a method of high volume, low cost manufacture. Such manufacturing criteria are particularly significant with respect to urinary retention catheters since tolerances are critical yet the cost of the resulting product must be consonant with the disposable nature of the product.

The invention disclosed herein relates to a novel urinary retention catheter and the method of manufacturing such a catheter.

2. Prior Art

In an attempt to satisfy the varius and conflicting criteria heretofore discussed, the prior art reflects an evolution of catheter designs. For several decades, all urinary retention catheters were manufactured by a dipping process wherein two longitudinally adjacent wires were dipped in a latex bath until a catheter tube of the desired diameter was built up. Subsequently a hole was pierced through the wall of the tube at one end and communicated with the cavity formed by one of the two wires, which cavity would later be the inflation lumen. Thereafter, a release agent was deposited around the tube in the area of the hole and the end of the tube was again dipped to build up another layer of latex at the end of the tube and which would constitute the balloon.

The catheter which resulted from this method of manufacture was widely accepted. However, certain disadvantages of the catheter constructed by this method of manufacture have been recognized. One disadvantage arises from the dipping process whereby precise dimensional control of the catheter diameter tends to be problemsome which, in turn, tends to increase the manufacturing cost.

While the strength and elasticity of latex rubber renders that material ideal as a catheter material, it has been found that, as do most materials, it poses a degree of susceptibility to encrustation from the salts commonly found in urine. On the other hand, recent developments in materials technology have made available the silicon rubbers which promise to be relatively free of susceptibility to encrustation.

Thus, more recent prior art catheter constructions have embodied silicon rubber tubes for the tip and body to relieve the encrustation problem and to enjoy a further advantage of compatibility with human tissue.

Although the prior art has established that silicone rubber is an acceptable material for a catheter, the problem still remains as to the structure of the catheter and the method of manufacturing a particular structure. The problems associated with prior art silicone rubber catheter constructions is exemplified by the catheter construction disclosed by Birtwell in U.S. Pat. No. 3,547,126. The Birtwell construction employs an extruded silicone tube as the body of the catheter in combination with a molded silicone tip which is provided with a rearwardly extending portion. The rearwardly extending portion is attached to the catheter tube of body and forms the inflation balloon. The tip portion, which is abuttingly affixed to the tube or body portion, is provided with a drainage lumen that must be aligned with the drainage lumen in the body of the catheter. Because of this construction, a number of problems arise both in the manufacture of the catheter and in the use thereof. For example, as previously stated, it is desired that the pressure required to inflate a balloon should be as low as possible and thus the balloon material should be soft and relatively elastic. However, in a catheter construction of the type disclosed by Birtwell, the tip and balloon are molded as one piece and, therefore, the tip will have the same mechanical properties as the balloon. Since the tip extends longitudinally substantially beyond the end of the extruded tube and since the material used to form the tip will have a low modulus of elasticity in order to insure that the balloon is easily inflated, the tip may deflect and bend during insertion, i.e., the tip portion does not possess the required rigidity. Moreover, in the Birtwell construction any bending of the tip is especially deleterious because of the glued, butt joint connection between the tip and the body, i.e., any bending of the tip will tensionally stress the bond between the tip and the body with the probable result of a failure of the bond.

Finally, because the tip in the Birtwell construction includes a drainage lumen, assembly of the tip and the tube is exacting if a misalignment is to be avoided. The problem of avoiding a misalignment during the assembly of the tip and the tube is economically significant since the avoidance of such misalignment requires that one must resort to either a manual assembly or a sophisticated mechanical assembly.

Another manufacturing difficulty associated with catheters of the type disclosed by Birtwell relates to the problems of the bond between the tip and the tube. More particularly, since this bond is essentially a butt joint, an adhesive of extraordinary strength is required. Indeed, in practice, it has been found to be difficult to locate any adhesive which is sufficiently strong to withstand the stresses to which this joint is subjected. In addition, however, even if an adhesive of sufficient strength is employed, it has been found that when the adhesive sets the tip is often longitudinally misaligned with the tube. While the cause of the misalignment phenomenon is not clearly understood, it is believed that the problem may arise from either an uneven amount of adhesive being initially deposited on the tip or, alternatively, from an uneven drying or curing of the adhesive. In any event, the problem is manifest and is present almost to the point of precluding economic manufacture of such a construction.

The problems associated with the prior art catheters described above are substantially reduced by the catheter and method of manufacture disclosed by Shoney in U.S. application Ser. No. 358,309, filed May 8, 1973, now U.S. Pat. No. 3,865,666. The Shoney construction provides a catheter where one end of the balloon is insert molded onto the catheter shaft while the other end of the balloon is fixed to either the catheter shaft or tip by conventional techniques, i.e., by adhesive bonding. In the preferred embodiment of Shoney the proximal end of the balloon is insert molded onto the catheter shaft and then the distal end is adhesively bonded onto the catheter tip by conventional technique after the tip has been insert molded onto the catheter shaft. It will be appreciated that even the preferred embodiment of Shoney suffers from the disadvantage that the distal end of the balloon must be bonded onto the tip of the catheter by a separate expensive and time consuming step. Further, the adhesive bond is a potential site for weakness in the catheter construction which is desirably eliminated.

The catheter construction disclosed hereinafter and the method of manufacture substantially overcome the problems associated with the prior art catheters and their method of manufacture.

SUMMARY OF THE INVENTION

An elastomeric catheter shaft with the proximal end of a balloon attached thereto, preferably by insert molding, is inserted into a mold. The shaft includes a drainage lumen extending longitudinally for the entire length thereof and an inflation lumen which extends longitudinally of the shaft for at least a major portion thereof, and communicates with the exterior of the shaft through an aperture located distally of the point of attachment of the balloon.

Within a mold, a hollow tip is insert molded onto the distal end of the shaft and simultaneously the distal end of the balloon is insert bonded onto the catheter tip. At least one drainage eye is provided through the tip and communicates with the cavity therein.

DESCRIPTION OF THE DRAWINGS

FIG. 1 is a view of the distal end of a partially constructed catheter.

FIG. 1A is a view, in section, taken along the section lines 1a—1a of FIG. 1.

FIG. 2 is a view of the distal end of the preferred embodiment of my invention.

DESCRIPTION OF THE PREFERRED EMBODIMENTS

Figure 3:
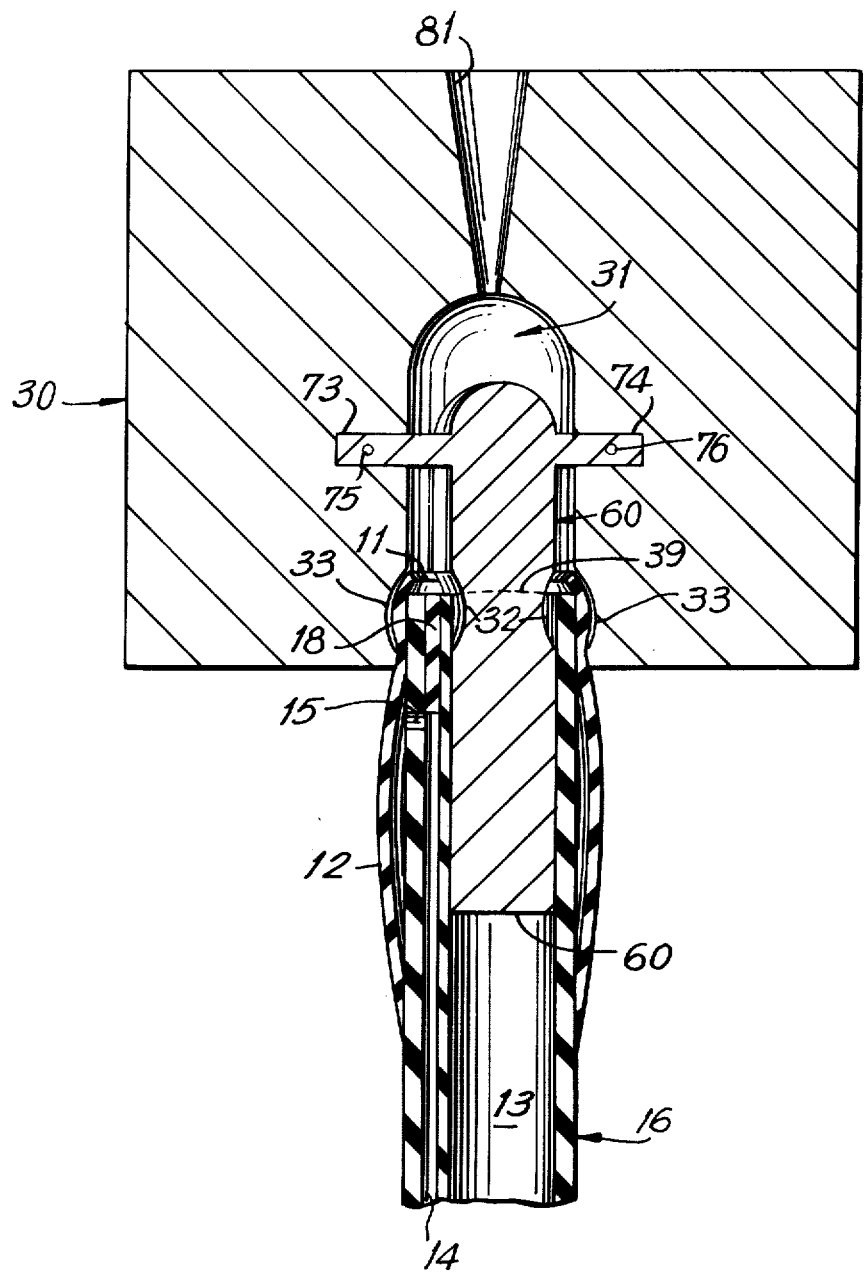
FIG. 3 is a view, in section of the mold, with catheter placed therein, used in my invention.

Referring to FIG. 1, there is shown, in section, the distal end of a partially constructed catheter for use in the preferred embodiment of my invention. It will be observed that the catheter shaft 16 includes a drainage lumen 13 and an inflation lumen 14. The shaft is made of an elastomeric material and, preferably, is made of extruded silicone rubber.

The shaft 16 is provided with an inflation lumen 14 which extends substantially for the entire longitudinal length of the shaft 16 and is further provided with an aperture 15 adjacent to the distal end 11 of the shaft. The aperture 15 provides communication from the inflation lumen 14 to the exterior of the shaft 16 and the interior of balloon 12. Preferably, the inflation lumen 14 is plugged by material 18 between the aperture 15 and the distal end 11 of the shaft 16.

The proximal end of balloon 12 is attached to the shaft, preferably by insert molding, as described in Shoney, supra, which disclosure is incorporated herein as reference. While insert molding the balloon to the shaft is preferred it is to be understood that any method, i.e., adhesive bonding, may be employed to attach the proximal end of the balloon 12 to the catheter shaft 16.

Referring now to FIG. 3, there is shown an apparatus, with shaft and balloon inserted therein, which may be used to practice my invention. Specifically, there is shown a mold 30 having a cavity 31 with a guide 60 disposed therein. As described in Shoney, supra, the guide is preferably provided with two transverse members 73 and 74 provided with holes 75 and 76, respectively. As shown in FIG. 3, the combination of the guide 60 and the catheter shaft 16 with balloon 12 attached thereto is placed within the cavity 31 of mold 30. The mold is constructed to receive the transverse extending members 73 and 74 and is preferably provided with pins inserted into holes 75 and 76 to insure proper alignment of guide 60.

In FIG. 3 it will be noted that the distal end of balloon 12 as well as the distal end of catheter shaft 16 and guide are disposed within the cavity 31 of mold 30. Preferably the balloon 12 is disposed so that the length of the balloon extending past the distal end of the catheter shaft 16 into the mold cavity 31 is not more than about the width of the wall of the distal end 11 of the catheter shaft 16 at its narrowest cross section and not less than about one half the width of the wall of the distal end 11 of the catheter shaft 16 at its narrowest cross section. It will be observed in this regard upon reference to FIG. 1A that the wall cross section of the distal end 11 of the catheter shaft designated by guide lines W—W preferably varies in order to accommodate inflation lumen 14. With this disposition of the components, the mold 30 is closed and an uncured elastomeric material is supplied, under pressure through supply channel 81. Preferably the material thus supplied is a catalyzed heat curable silicone rubber. In the event that such a heat curable material is used, the mold 30 is heated by an appropriate means, until the supplied material is at least partially cured. When at least a partial curing thereof has been achieved, the mold 30 is opened and the catheter and guide 60 are removed therefrom. The guide 60 is removed from the catheter by stretching the tip 20 and pushing the guide 60 out through the two apertures, 21 and 23, which were defined by the transverse members 73 and 74.

When the guide has been removed, the catheter shown in FIG. 2 remains. Referring to FIG. 2 it will be seen that a hollow tip 20, containing drainage apertures 21 and 23, has been provided that is molded and bonded to the distal end of the catheter shaft 16. The cavity 22 within the tip 20 is aligned with and forms an extrusion of the drainage lumen 13. These features, of course, are provided for by Shoney, but the present invention has the additonal advantage that the balloon 12 is insert bonded into the tip 20 thereby avoiding the necessity of a separate step to bond the balloon 12 onto the tip 20.

It will be recalled that the length of balloon 12 extending past the distal end 11 of the catheter shaft 16 is preferably not more than about the width of the wall of the distal end 11 of the catheter shaft 16 at its narrowest cross section. The reason for this is that when elastomeric material is injected into the mold cavity 31 the pressure of the injected material causes the balloon 12 to distent inwardly into the cavity with the result that the annular passage way to the catheter shaft 16 is partially blocked. As may be appreciated, as the length of balloon 12 extending into the mold cavity 31 increases the tendency of the distended balloon 12 to block the annular passageway to the distal end of catheter shaft 16 also increases. The effect of this blockage is to decrease the rate at which the elastomeric material may be injected into the mold cavity 31 and in extreme circumstances may substantially impede the creation of an adequate bond between the tip 20 and catheter shaft 16. Therefore, in order to minimize the tendency of the balloon 12 to block the annular passageway in the mold cavity 31 and to insure adequate bonding between the tip 20 and the shaft 16 it is preferred that the balloon extend beyond the distal end of the distal end 11 of the catheter shaft 16 not more than about the width of the wall of the distal end of the catheter shaft at it narrowest cross section.

It will also be recalled that the length of balloon extending beyond the distal end 11 of the catheter shaft 16 is preferably not less than about one half the width of the wall of the distal end of the catheter shaft at its narrowest cross section. The reason for this is that the strength of the bond between the balloon 12 and the catheter tip 20 is related to the length of the balloon 12 injection bonded into the catheter tip 20. That is, as the length becomes shorter the bond becomes weaker. As a result, in order to insure adequate bond strength it is preferred that the balloon extend beyond the distal end of the catheter shaft at least about one half the width of the wall of the distal end of the catheter shaft at its narrowest cross section.

The problems associated with the length of the balloon extending beyond the distal end 11 of the catheter shaft 16 are diminished by other features of my invention. Referring to FIG. 3 it will be noted that guide 60 may be provided with generally arcuate notches 32. The purpose of these notches is to provide a larger annular space for the passage of injected elastomeric material to the distal end 11 of the catheter shaft 16. Additionally, the arcuate notches 32 may be designed as is shown in FIG. 3 so as to extend proximally of the distal end of the distal end of the catheter shaft 16 so as to provide for additional bonding between the tip 20 and the catheter shaft 16 along the longitudinal axis of the catheter shaft.

Additionally mold 30 may be provided with generally arcuate notches 33 as shown in FIG. 3. The purpose of these notches is to enhance the strength of the bond between the catheter tip 20 and the balloon 12 by providing for bonding between the tip and balloon proximally of the distal end 11 of catheter shaft 16.

It is to be understood that the term "generally arcuate notches" encompasses notches which first widen outwardly gradually and then narrow inwardly gradually so as to provide for relatively gradual smooth areas of transition. It is also to be understood, however, that while generally arcuate notches are preferred, other configurations may be employed. For instance, rectangular notches are contemplated as within the scope of my invention.

The flow of uncured elastomeric material through mold cavity 31 may also be enhanced by terminating guide 60 at dotted line 39 as shown in FIG. 3. It will be appreciated that by so terminating guide 60 the uncured elastomeric material may easily flow around distended balloon 12 to create the bond between the tip 20 and catheter shaft 16. It will further be appreciated, however, that the resulting tip 20 will be solid and will not contain a drainage eye. The drainage eye must therefore be subsequently punched longitudinally through the tip so as to provide communication with drainage lumen 13.

With general regard to all of the embodiments of my method heretofore described, it is preferable to employ an extruded catheter shaft which is only partially cured. Additionally, when the balloon and the tip are molded onto the shaft, it is preferable to only partially cure the balloon and the shaft. It is preferable to only partially cure the balloon and tip and to use a partially cured shaft in order that the resulting product may be cured (post-cured) as a unit. Such a post-curing had been found to provide a stronger unitary product.

With respect to materials, it is preferred to use silicone rubber for the shaft, tip and the balloon. Additionally, in the event the balloon is not insert molded onto the shaft the preferable agent for bonding the balloon to the shaft is a catalyzed, uncured, heat curable silicone rubber.

Finally, those skilled in the catheter art will appreciate that unitary retention catheters are generally provided with two funnels at the proximal end of the shaft, one funnel associated with the drainage lumen and one associated with the inflation lumen. Such funnels, and the method by which they are attached to the catheter shaft, are well known, e.g., Birtwell discloses such a pair of funnels.

It will be understood that by the present invention there is provided a retention catheter of the Foley type which requires a minimum number of steps to manufacture. Further, there is provided a catheter of the Foley type characterized by strong bonds between the balloon, tip and shaft. It will further be understood that while the invention has been described with respect to preferred embodiments, variations may be perceived by those skilled in the art while nevertheless not departing from the scope of my invention as described by the claims appended hereto.

I claim:

1. In a process for manufacturing a retention catheter having a distal end and a proximal end which comprises:
   a. forming an elastomeric catheter shaft with a balloon sleeve surrounding said shaft and attached thereto and having a drainage lumen extending longitudinally thereof, and an inflation lumen extending longitudinally for at least a major portion thereof and communicating with the exterior of said shaft through an aperture adjacent the distal end of said shaft, said balloon being attached at its proximal end on the proximal side of said aperture;
   b. inserting a guide in the drainage lumen of said shaft to support the distal end of said shaft;
   c. inserting at least a portion of said shaft, including at least a portion of said guide and a distal portion of said balloon sleeve, in a mold;
   d. injection molding a curable elastomer into a cavity between said mold and said guide so as to abut the distal end of said shaft with said elastomer and so as to mold said elastomer about the distal end of said balloon sleeve;
   e. curing said elastomer, and removing said catheter and guide from said mold and said guide from said catheter, thereby forming a catheter tip bonded to said shaft and bonded about said balloon;
   f. providing at least one drainage eye through said tip and communicating with said drainage lumen.

2. The process of claim 1 wherein the tip is molded to both the distal end and a portion of the inside surface of said shaft.

3. The process of claim 1 wherein the tip is molded about the balloon both proximally and distally of the distal end of said catheter shaft.

4. The process of claim 1 wherein the length of balloon extending distally of the distal end of the catheter shaft is not greater than about the width of the wall of the distal end of the catheter shaft at its narrowest cross section.

5. The process of claim 1 wherein the width of the annular space along the longitudinal axis of the mold cavity is varied at the portion of the mold cavity wherein the balloon is distended inwardly.

6. The process of claim 1 wherein said tip molded in step (d) is hollow and said at least one drainage eye is provided simultaneously with step (d).

7. The process of claim 1 wherein said tip insert molded in step (d) is solid and said at least one drainage eye communicating with said drainage lumen is subsequently punched through said tip.

8. The process of claim 1 wherein said shaft, said tip and said balloon are silicone rubber.

9. The process of claim 1 wherein said balloon is attached to said catheter shaft by insert molding.

10. The process of claim 1 wherein the length of balloon extending distally of the distal end of the catheter shaft is not less than about one half the width of the wall of the distal end of the catheter shaft at its narrowest cross section.

11. The process of claim 10 wherein the length of balloon extending distally of the distal end of the catheter shaft is not greater than about the width of the wall of the distal end of the catheter shaft at its narrowest cross section.

* * * * *